United States Patent

Gosteli et al.

Patent Number: 4,990,618
Date of Patent: Feb. 5, 1991

[54] PROCESS FOR THE PRODUCTION OF 4,5,6,7-TETRAHYDROTHIENO-[3,2-C]-PYRIDINES

[75] Inventors: Jacques Gosteli, Basel; Aleksander Warm, Visp, both of Switzerland

[73] Assignee: Lonza Ltd., Gampel/Valais, Switzerland

[21] Appl. No.: 517,729

[22] Filed: May 2, 1990

Related U.S. Application Data

[62] Division of Ser. No. 409,743, Sep. 20, 1989.

[30] Foreign Application Priority Data

Sep. 23, 1988 [CH] Switzerland ............... 3539/88

[51] Int. Cl.$^5$ ................ C07C 211/22; C07C 211/44
[52] U.S. Cl. .................................. 546/221; 546/242
[58] Field of Search .................... 546/114, 221, 242

[56] References Cited

FOREIGN PATENT DOCUMENTS 2404308  1/1974  Fed. Rep. of Germany .

OTHER PUBLICATIONS

"Ticlopidine: A Review of its Pharmacodynamic and Pharmacokinetic Properties, and Therapeutic Efficacy in Platelet—Dependent Disease States", by Emmanuel Saltied and Alan Ward, Drugs, vol. 34, 1987, pp. 222–262.

"Thiophene Isosters of Isoquinoline", by Salo Gronowitz and Elina Sandberg, Arkiv for Khemi, vol. 32, No. 19, (1971), pp. 217–227.

"Piperidine Derivatives. XV. The Preparation of 1—Benzoyl—3—Carbethoxy—4—Piperidene. A Synthesis of Guvaeine", S. M. McElwain & Gilbert Strole, Jour. of Am. Chem. Soc., vol. 68, Jan.—Jun. 1946, pp. 1049 to 1053.

"Synthese Des Thienopyridines", by F. Eloy and A. Deryckere, Bulletin Des Societes Chemiques Belges, vol. 79, (1970), Mai, Juin Issue, pp. 301–311.

Primary Examiner—Alan L. Rotman
Assistant Examiner—Joseph K. McKane
Attorney, Agent, or Firm—Fisher, Christen & Sabol

[57] ABSTRACT

The following intermediate compounds, namely, 4-Oxo-3-(2-propenyl)-piperidine-3-carboxylic acid ester of the formula:

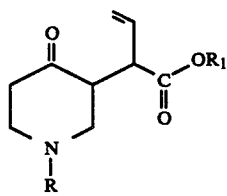

wherein R is hydrogen, a formyl group, an acetyl group or a benzoyl group or is a benzyl group, whose aromatic ring optionally is ring-substituted by at least one halogen atom, and $R_1$ is an alkyl group with 1 to 4 C atoms.

4-Oxo-3-(2-propenyl)-piperidine of the formula:

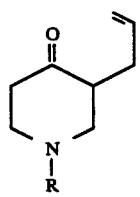

wherein R is hydrogen, a formyl group, and acetyl group or a benzoyl group or is a benzyl group, whose aromatic ring optionally is ring-substituted by at least one halogen atom.

2 Claims, No Drawings

PROCESS FOR THE PRODUCTION OF 4,5,6,7-TETRAHYDROTHIENO-[3,2-c]-PYRIDINES

This is a divisional of application Ser. No. 409,743, of Jacques Gostelli et al., filed on Sept. 20, 1989.

BACKGROUND OF THE INVENTION

1. Field Of The Invention

The invention relates to a process for the production of 4,5,6,7-tetrahydrothieno-[3,2-c]-pyridines of the formula:

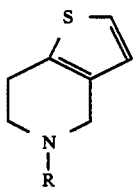

wherein R is hydrogen, a formyl group, an acetyl group or a benzoyl group or is a benzyl group, which optionally is ring-substituted by at least one halogen atom. Compounds of said type have antithrombotic action by preventing blood platelet aggregation [E. Saltiel et al., Drugs, 34 (1987), p. 222].

2. Background Art

Numerous processes are known for the production of thienopyridine derivatives. Thus, a synthesis is described in West German Patent No. 2,530,516 in the course of which bromination of an alkyl group in allyl position with N-bromosuccinimide is described. But such reactions are hardly feasible on an industrial scale.

Other production methods are described in Bull. Soc. Chim. Belgique, 79, (1979), p. 301, as well as in Arkiv Kemi., 32, (1970), pp. 217 and 249. In said reaction sequences, which take place over five or six reaction steps, acids or complex alkali metal hydrides are used. This indeed is feasible on a laboratory scale but cannot be transferred to an industrial scale. In addition, the high costs of the reagents used cause both processes to not make any economical sense. Further, the yields are very small.

Derivatives of 4,5,6,7-tetrahydrothieno-[3,2-c]-pyridine, their use in pharmaceutical agents and a process for their production have already been described in West German Patent 2,404,308. In such process, compounds of the formula:

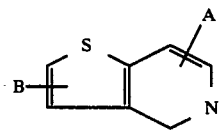

wherein A and B each stand for at least one atom or a group of the class consisting of hydrogen atoms, halogen atoms, hydroxyl groups, lower alkyl radicals, lower alkoxy radicals, nitrogen groups and amino groups, are condensed with a halide of the formula Hal-R, in which Hal is a halogen atom and R is an optionally substituted alkyl radical, aryl radical or aralkyl radical, with formation of a pyridinium salt of the formula:

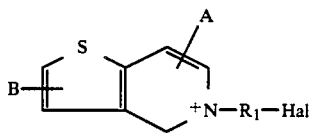

and then such pyridinium salt is hydrogenated to the derivative of formula (1). But such process is expensive and difficult to perform, since it requires numerous and difficult process steps.

BROAD DESCRIPTION OF THE INVENTION

The object of the invention is to avoid the above-described drawbacks and to make available a simple process for the production of said pyridine derivatives.

The starting point of the process according to the invention is the 4-oxo-piperidine-3-carboxylic acid esters of the general formula:

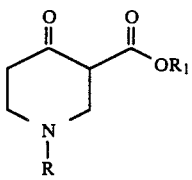

wherein R is hydrogen, a formyl group, an acetyl group or a benzoyl group or is a benzyl group, which optionally is ring-substituted by at least one halogen ring, and $R_1$ stands for an alkyl group having 1 to 4 C atoms. These compounds are accessible by the synthesis described by McElvain et al. in J. Am. Chem. Soc., 68, (1946), p. 1049, starting from ammonia and acrylic acid esters.

In the first step the 4-oxo-piperidine-3-carboxylic acid ester is converted, with an allylhalide in the presence of a base, to the as yet undescribed 4-oxo-3-(2-propenyl)piperidine-3-carboxylic acid esters of the formula:

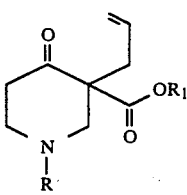

wherein R and $R_1$ have the above-stated meaning. By allylhalide is suitably meant the corresponding chloride, bromide or iodide. As bases there can be used alkali hydrides, such as, sodium or potassium hydride, alkali alcoholates, such as, sodium, potassium tert-butylate, or also alkali carbonates or alkali hydroxides in combination with a suitable solvent intensifying the basicity, such as, dimethylformamide. Suitably the operation is performed in the presence of a solvent which is inert with the bases used. Advantageously the operation can be conducted under inert gas, such as, nitrogen or argon. The reaction temperature suitably varies between 0° C. and the boiling point of the selected solvent. The resultant 4-oxo-3-(2-propenyl)-piperidine-3-carboxylic acid ester can be worked up in a usual way and then fed to the next step.

In an alternative embodiment, a start can be made from a 3,3'-iminodipropionic acid ester of the formula:

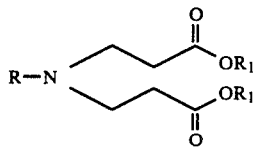

wherein R and R₁ have the above-stated meanings, a precursor of the 4-oxo-piperidine-3-carboxylic acid ester, and, without isolation of the latter compound, the 4-oxo-3-(2-propenyl)piperidine-3-carboxylic acid ester can be achieved directly. This alternative embodiment is preferred. Especially preferred is to start from the corresponding 3,3'-iminodipropionic acid tert-butyl ester, which in the presence of potassium tert-butylate and with allylbromide in an inert solvent is directly converted to the corresponding 4-oxo-3-(2-propenyl)-piperidine-3-carboxylic acid tert-butyl ester. Without isolation of such intermediate, the next step can follow.

The 3,3'-iminodipropionic acid tert-butyl ester, for its part, can be produced from ammonia by reaction with tert-butyl acrylate in a first step and further reaction in a second step with the corresponding halide of the formula:

wherein R has the above-stated meaning and Hal is chlorine or bromine.

The next step comprises the removal of the ester function by decarboxylation and conversion to the as yet undescribed 4-oxo-3-(2-propenyl)-piperidine-3-carboxylic acid of the formula:

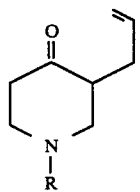

wherein R has the above-stated meaning. Removal of the ester group is successfully performed with decarboxylation agents known to one skilled in the art. These agents include acids, such as, hydrochloric acid, sulfuric acid, methanesulfonic acid or p-toluenesulfonic acid, or bases, such as, alkali hydroxides or alkali alcoholates, or also strong nucleophilicity such as, thiolates, alkali halides or cyanides, optionally in combination with a solvent intensifying the nucleophiles (e.g., dimethyl sulfoxide, dimethylformamide, hexamethylphosphoric acid triamide or N,N'-dimethylpropylene urea). Preferably thiolates in combination with hexamethylenephosphoric acid triamide or dimethylpropylene urea are used. Suitable thiolates are especially the alkali alkanethiolates, such as, sodium-1-propanethiolate.

If according to the especially preferred process a tert-butyl group appears as the ester function, diluted aqueous hydrochloric acid has proved especially suitable as the decarboxylation agent.

The reaction temperature depends on the decarboxylation agent used. When thiolates are used, the operation is suitably performed between 0° and 40° C., preferably at room temperature. When hydrochloric acid is used, the operation is suitably performed at reflux temperature.

Working up of the 4-oxo-3-(2-propenyl)-piperidine can take place according to usual laboratory methods.

The third step of the process according to the invention comprises the reaction of the 4-oxo-3-(2-propenyl)-piperidine in the presence of an acid with ozone and then reduction to 4-oxo-3-piperidine acetaldehyde of the formula:

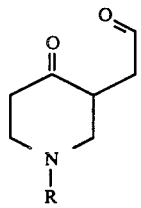

wherein R has the above-stated meaning.

All agents which are suitable for forming a salt with the amine are useful as the acids. Especially advantageous agents are trifluoroacetic acid, methanesulfonic acid or hydrogen chloride.

A reduction agent known to one skilled in the art is added to convert the ozonides resulting after the ozonization to the desired aldehyde. Suitable agents are, for example, triphenylphosphine, sodium borohydride, hydrogen sulfites, thiosulfates or dialkylsulfides. Dimethyl sulfide is especially suitable.

Ozonization is advantageously performed at a temperature between $-70°$ and $+40°$ C. in an inert gas atmosphere and in the presence of an inert solvent.

The resultant 4-oxo-3-piperidine acetaldehyde can be isolated by usual laboratory methods but advantageously cyclization to the end product is performed in situ with hydrogen chloride and hydrogen sulfide in the presence of a metal halide. By metal halides are suitably meant the chlorides, bromides or iodides of tin, zinc or titanium. Preferably titanium tetrachloride, tin tetrachloride or zinc dibromide are used. As a solvent the one from the preceding ozonization is generally used. Cyclization suitably takes place at a temperature between $-70°$ and $+40°$ C., preferably between $-20°$ and $+20°$ C.

After the reaction is completed, the desired 4,5,6,7-tetrahydrothieno-[3,2-c]-pyridinecan be worked up and purified in a usual way.

DETAILED DESCRIPTION OF THE INVENTION

EXAMPLE 1

(al) Production of ethyl-1-benzoyl-4-oxo-3-(2-propenyl-3-piperidine carboxylate 1.16 g (4.22 mmol) of ethyl-1-benzoyl-4-oxo-3-piperidine carboxylate, 9 ml of tert-butanol and 0.57 g (4.93 mmol) of potassium tert-butylate (97 percent) were used at 25° C. and stirred for 30 minutes. Then 0.70 g (5.67 mmol) of allylbromide was instilled in 2 minutes. The mixture was stirred with reflux for 16 hours, the reaction mixture was concentrated by evaporation and divided between 30 ml of methylene chloride and 30 ml of water. The emulsion was adjusted to pH 7 with hydrochloric acid (1N). The phases were separated and the aqueous phase was extracted three more times with 30 ml of methylene chloride. The combined organic phases was dried with magnesium sulfate and concentrated by evaporation. 1.34 g of crude product was obtained which was purified by column chromatography. The yield was 0.850 g of pure ethyl-1-benzoyl-4-oxo-3-(2-propenyl)-3-piperidine carboxylate, which equals 64 percent. Data concerning the compound was:

$^1$H-NMR: (CDCl$_3$, 300 MHz) δ in ppm 7.45, s, 5H 5.70, bs, 1H 5.07, d, J=10 Hz, 2H 4.60, bs, 2H 4.18, m, 2H 3.32, m, 2H 2.83, ddd, J=15 HZ, 11 Hz, 6.5 Hz, 1H 2.52, bs, 3H 1.26, t, J=7.5 Hz, 3H.

(a2) Production of ethyl-1-[2(-chlorophenyl)methyl]-4-oxo-3-(2-propenyl)-3-piperidine carboxylate 20.00 g (0.067 mol) of ethyl-1-[(2-chlorophenyl)methyl]4-oxo-3-piperidine carboxylate was put into 50 ml of tert-butanol and warmed to 30° C. Then 8.53 g (0.074 mol) of potassium tert-butylate was dissolved in 50 ml of tert-butanol and warmed to 45° C. This solution was instilled at 30° C. in 2 minutes into the educt present and stirred for 1 more hour at 30° C. Then 8.50 g (0.67 mol) of allylbromide was instilled in 10 minutes at 30° C. and stirred for another 2 hours at 30° C. The reaction mixture was completely concentrated by evaporation on a Rotavapor. The solid residue was mixed with 100 ml of water and 100 ml of ether. The phases were separated and the basic water phase was extracted twice more with 50 ml of ether. Then the combined ether phases were washed once with 50 ml of saturated sodium sulfate solution. Organic phases were dried with magnesium sulfate and evaporated. A yellow oil resulted. The yield was 20.85 g of ethyl-1-[(2-chlorophenyl)methyl]-4-oxo-3-(2-propenyl)-3piperidine carboxylate, which equals 91.8 percent. Data concerning the compound was:

$^1$H-NMR: (CDCl$_3$, 300 MHz) δ in ppm 7.48, d, J=7.5 Hz, 1H 7.37, d, J=7.5 Hz, 1H 7.25, q, J=7.5 Hz, 2H 5.86–5.72, m, 1H 5.03, d, J=17 Hz, 1H 5.02, d, J=11 Hz, 1H 4.29–4.07, m, 2H 3.70, s, 2H 3.45, dd, J=12.5 Hz, 2.5 Hz, 1H 3.10–3.02, m, 1H 2.96–2.84, m, 1H 2.58–2.31, m, 5H 1.23, t, J=7.5 Hz, 3H.

(a3) Production of methyl-1-[(2-chlorophenyl)methyl]-4-oxo-3-(2-propenyl)-3-piperidine carboxylate 14.60 g (51.8 mmol) of methyl-1-[(2-chlorophenyl)-methyl]-4-oxo-3-piperidine carboxylate was dissolved in 40 ml of tertbutanol and warmed to 30° C. Within 2 minutes 6.57 g (58.4 mmol) of potassium tert-butylate in 45 ml of tert-butanol was added. After 15 minutes of stirring, 25 ml of tert-butanol was added once more. Then 6.34 g (51.4 mmol) of allylbromide was added within 10 minutes and stirred for 2 more hours at 30° to 35° C. The reaction mixture was concentrated by evaporation and 70 ml of water and 70 ml of ether were added to the residue. The organic phase was washed with 50 ml of sodium sulfate solution, dried on magnesium sulfate and concentrated by evaporation. The yield was 40.68 g of methyl1-[(2-chlorophenyl)methyl]-4-oxo-3-(2-propenyl)-3-piperidine carboxylate, which equals 88.1 percent. Data concerning the compound was:

$^1$H-NMR: (CDCl$_3$, 300 MHz) δ in ppm 7.47, d, J=7.5 Hz, 1H 7.37, d, J=7.5 Hz, 1H 7.25, q, J=7.5 Hz, 2H 5.85–5.71, m, 1H 5.03, d, J=17 Hz, 1H 5.02, d, J=11.5 Hz, 1H 3.71, s, 5H 3.43, dd, J=11 Hz, 2.5 Hz, 1H 3.09–3.02, m, 1H 2.95–2.84, m, 1H 2.58–2.50, m, 2H 2.47–2.32, m, 3H.

(b) Production of 1-[(2-chlorophenyl)methyl]-3-(2-propenyl)-4-piperidine 0.37 g (1.15 mmol) of methyl-1-[(2-chlorophenyl)methyl]-4-oxo-3-(2-propenyl)-3-piperidine carboxylate, 0.331 g (3.52 mmol) of sodium-1-propanethiolate and 7 ml of hexamethylphosphoric acid triamide were placed under argon and stirred for 2 hours at room temperature. The reaction solution was acidified with 10 ml of hydrochloric acid 1N, then washed with 5 ml of ether 3 times and adjusted to pH 9 by addition of sodium carbonate solution (10 percent in water). Then it was extracted with 35 ml of ether, and the ether phase was washed 3 times with 5 ml of water and 5 ml of sodium sulfate solution, dried on magnesium sulfate and concentrated by evaporation. The yield was 0.225 g of 1-[(2chlorophenyl)methyl]-3-(2-propenyl)-4-piperidine, which equals 74 percent. Data for the compound was:

$^1$H-NMR: (CDCl$_3$, 300 MHz) δ in ppm 7.52, d, J=7.5 Hz, 1H 7.38, d, J=7.5 Hz, 1H 7.25, q, J=7.5 Hz, 2H 5.80–5.56, m, 1H 5.00, d, J=19 Hz, 1H 4.98, d, J=10. Hz, 1H 3.73, 3.72, 2d, AB, J = 14.5 Hz, 2H 3.13–2.98, m, 2H 2.66–2.50, m, 4H 2.45–2.32, m, 2H 2.08, dt, J=15 Hz, 7.5, 1H.

(c) Production of 1-[2-chlorophenyl)methyl]4-oxo-3-piperidine acetaldehyde 8.1 g (30.7 mmol) of 1-[(2-chlorophenyl)methyl]-3-(2-propenyl)-4-piperidine was placed in 85 ml of methylene chloride under argon and the solution was cooled to −60° to −70° C. 7.15 g (61.4 mmol) of trifluoroacetic acid in 15 ml of methylene chloride was added within 10 minutes. Then ozone was introduced until the solution exhibited a greenish blue coloring. The excess ozone was removed by passing nitrogen through. Then a solution of 2.36 g (36.8 mmol) of dimethyl sulfide in 10 ml of methylene chloride was added. After 5 minutes stirring at −60° to −70° C., it was warmed to 0° C. The reaction mixture was concentrated by evaporation and 300 ml of ether, 150 ml of water and 4.2 g of sodium carbonate solution (pH 8) was added to the residue.

The organic phase was separated, washed 3 times with 50 ml of water and 50 ml of sodium carbonate solution, dried over magnesium sulfate and then concentrated by evaporation. The yield was 7.07 g of 1-[(2-chlorophenyl)methyl]-4-oxo-3-piperidine acetaldehyde, which equals: 76 percent. Data concerning the compound was:

$^1$H-NMR: (CDCl$_3$, 300 MHz) δ in ppm 9.29, s, 1H 7.53, d, J=7.5 Hz, 1H 7.38, d, J=7.5 Hz, 1H 7.26, q, J=7.5 Hz, 2H 3.76, s, 2H 3.32-3.15, m, 3H 2.92, ddd, J=17, 5 Hz, 7.5 Hz, 1.5 Hz, 1H 2.72, td, J=14 Hz, 6 Hz, 1H 2.56, td, J=11.5 Hz, 4 Hz, 1H 2.38, dt, J=14 Hz, 2.5 Hz, 1H 2.34–2.22, m, 2H.

(d) Production of 5-[2-chlorophenyl)methyl]-4,5-6.7tetrahydrothieno-[3,2-c]-pyridine 0.97 g (3.68 mmol) of 1-[(2-chlorophenyl)methyl]-3-(2-propenyl)-4-piperidine was dissolved, under argon, in lo ml of methylene chloride and cooled to −60° to −70° C. Then 0.86 g (7.39 mmol) of trifluoroacetic acid in 2.5 ml of methylene chloride was instilled within 5 minutes. Then ozone was introduced until the solution showed a greenish blue color. The excess ozone was removed with nitrogen. Then a solution of 0.28 g (4.37 mmol) of dimethyl sulfide in 2.5 ml of methylene chloride was instilled within 5 minutes. After 5 minute stirring at −60° to 70° C., it was warmed to 0° C. 5 ml of methanol and then, within 5 minutes, a solution of 3.39 g (12.88 mmol) of tin tetrachloride in 5 ml of methylene chloride was added to this solution (exothermic). Introduction of hydrogen chloride began at 0° C., 5 minutes later the introduction of hydrogen sulfide began. The introduction was ended after 6 hours and stirring was continued for 10 hours. The reaction mixture was concentrated by evaporation. 75 ml of water, 75 ml of ether and sodium carbonate were added to the residue, until the pH of the mixture was about 9. The organic phase was separated, dried with magnesium sulfate and concentrated by evaporation. The yield was 0.903 g of 5-[2-chlorophenyl)methyl]-4,5,6,7-tetrahydrothieno-[3,2-c]-pyridine, which equals 73 percent. Data concerning the compound was:

$^1$H-NMR: (CDCl$_3$, 300 MHz) δ in ppm 7.54, d, J=7.5 Hz, 1H 7.36, d, J=7.5 Hz, 1H 7.20, q, J=7.5 Hz, 2H 7.06, d, J=5 Hz, 1H 6.70, d, J=5 Hz, 1R 3.83, s, 2H 3.64, s, 2H 2.88, m, 4H.

(e) Production of
5-[2-chlorophenyl)methyl]-4,5,6,7-tetrahydrothieno-[3,2-c]-pyridine 1.35 g (5.13 mmol) of tin tetrachloride was placed in 10 ml of chloroform. Then 0.39 g (1.47 mmol) of 1-[(2-chlorophenyl)methyl]-4-oxo-3-piperidine acetaldehyde, dissolved in 15 mol of chloroform, was added to it. After cooling to −15° C., introduction of hydrogen chloride and introduction of hydrogen sulfide began. The introduction ended after 6 hours. It was stirred for 10 hours at room temperature. The reaction mixture was concentrated by evaporation. 30 ml of water, 30 ml of ether and 1.5 g of sodium carbonate (pH 8–9) were added. The organic phases was separated, dried on magnesium sulfate and concentrated by evaporation. The yield was 0.27 g of 5-[(2-chlorophenyl)methyl]-4,5,6,7-tetrahydrothieno-[3,2-c]-pyridine, which equals 70 percent. Data concerning the compound was:

$^1$H-NMR: (CDCl$_3$, 300 MHz) δ in ppm 7.54, d, J=7.5 Hz, 1H 7.36, d, J=7.5 Hz, 1H 7.20, q, J=7.5 Hz, 2H 7.06, d, J=5 Hz, 1H 6.70, d, J=5 Hz, 1H 3.83, s, 2H 3.64, s, 2H 2.88, m, 4H

EXAMPLE 2

(a) Production of di-tert-butyl 3,3'-iminodipropionate 112.8 g (0.88 mmol) of tert-butylacrylate was cooled to −60° C. and then mixed with 50 g (2.94 mol) of ammonia. The reaction mixture was stirred in an autoclave for 39 hours at 50° C. Then 32.04 g (0.25 mmol) of tert-butylacrylate was additionally added and again stirred for 4 days at 50° C. The excess tert-butylacrylate was recovered by extraction. 141.26 g of a mixture of tri-tert-butyl 3,3',3''-nitrilotripropionate (NR$_3$) and di-tert-butyl 3,3'-iminodipropionate (NR$_2$) in a ratio of 1:1.9 was obtained from the reaction mixture by extraction with ether. This corresponded to a yield of 92 percent relative to tert-butylacrylate. 500 ml of ether was added to this mixture (50 g) for separation and, after cooling to 0° C., 5 g (0.14 mol) of HCl gas was added. The resultant precipitate was filtered. 86.3 percent of NR$_2$ and 13.7 percent of NR$_3$ were obtained. The precipitate was then dissolved in 200 ml of water, made basic with 5N NaOH and extracted three times with 50 ml of ether. The combined ether phases were dried on MgSO$_4$ and concentrated by evaporation. The resulting amine mixture was again treated with 4 g of HCl. The precipitate was filtered. 99.6 percent and NR$_2$ was obtained. 27.23 g of the subtitle compound (noted above) was obtained from the precipitate as described. Data concerning the compound was:

$^1$H-NMR: (CDCl$_3$, 300 MHz) 3.85 (t, J=7.0 Hz, 4H) 2.43 (t, J=7.0 Hz, 4H) 1.61 (bs, 1H) 1.47 (s, 18H)

(b) Production of
di-tert-butyl-N-[(2-chlorophenyl)methyl]-3,3'-iminodipropionate 45.06 g (0.27 mol) of 2-chlorobenzylchloride and 51 g (0.19 mol) of di-tert-butyl-3,3'-iminodipropionate were dissolved in 350 ml of acetonitrile, mixed with 28.3 g (0.28 mol) of triethylamine and refluxed. After 5 hours, 8.85 g (0.06 :mol) of 2-chlorobenzylchloride and 9.34 g (0.09 mol) of triethylamine were again in added. After being refluxed for 15 hours, the reaction mixture was concentrated by evaporation. The residue was taken up in 300 ml of water, 100 ml of HCl 5n and 300 ml of ether. The acidic water phase was made basic with NaOH (20 percent) and extracted three times with 100 ml of ether. 67.7 g (91 percent) of the subtitle compound (noted above) was obtained from the ether phase. Data concerning the compound was:

$^1$H-NMR: (CDCl$_3$, 300 MHz) 7.5 (dd, J=8.0 Hz, 1.5 Hz, 1H) 7.32 (dd, J=8.0 Hz, 1.5 Hz, 1H) 7.26–7.14 (m, 2H) 3.7 (s, 2 H) 2.82 (t, J=7.5 Hz, 4H) 2.41 (t, J=7.5 Hz, 4H) 1.44 (s, 18H).

(c) Production of
1-[(2-chlorophenyl)methyl]-3-(2-propenyl)-4-piperidine 16.60 g (0.145 mol) of K-tert-butylate was introduced and warmed to 75 to 80.C. Then 50 g 0.125 mol) of di-tertbutyl-N-[(2-chlorophenyl)methyl]-3,3'-iminodipropionate in 100 ml of toluene was added within 10 minutes. After 20 minutes, the toluene was practically completely evaporated at 75° C. and 220 mbars. Then 400 ml of tert-butanol was added to 40° C. 17.94 g (0.145 mol) of allylbromide was added to the resulting suspension at 40° C. in 10 minutes. It was allowed to stir for 45 minutes more at 40° C. The reaction mixture was then completely concentrated by evaporation and then the solid residue was dissolved in 500 ml each of H$_2$O plus 300 ml of ether. The aqueous phase was again extracted twice with 100 ml each of ether. The combined ether phases was washed with 50 ml of saturated Na$_2$SO$_4$ and then concentrated by evaporation. Then 500 ml of 0.5 n HCl was added to the resulting oil and refluxed for 30 to 45 minutes (CO$_2$ development). The reaction mixture was cooled to room temperature and mixed again with 20 ml of HCl conc. It was extracted three times with 100 ml of ether and the ether phase was dried with MgSO$_4$ and evaporated. The acidic water phase was made basic with NaOH and extracted three times with 200 ml of ether. The ether phases were combined and dried with MGSO$_4$ and evaporated. A yellowish oil resulted. The yield was 28.66 g (87 percent). Data concerning the compound was: $^1$H-NMR: CDCl$_3$, 300 HMz) δ in ppm 7.52, d, J=7.5 Hz, 1H 7.38, d, J=7.5 Hz, 1H 7.25, m, 2H, 5.80–5.56, m, 1H 5,00, d, J=19.0 Hz, 1H 4.98, d, J=10.0 Hz, 1H 3.73, 3.72, 2d, AB, J =14.5 Hz, 2H 3.13–2.98, m, 2H 2.66–2.50, m, 4H 2.45–2.32, m, 2H 2.08, dt, J=15.0 Hz, 7.5 Hz, 1H.

MS: (E.I. 70 eV): 263 (M+, 2.2), 234 (12), 221 (17.2), 146 (25), 125 (100).

IR (Film): 3073, 2950, 2910, 2802, 2764, 1716.

(d) Production of
5-[(2-chlorophenyl)methyl]-4,5,6,7-tetrahydrothieno-[3,2-c]-pyridine 13.50 g (51.2 mmol) of 1-[(2-chlorophenyl)methyl]-3-(2-propenyl)-4-piperidine was placed under argon in 220 ml of methylene chloride and cooled to −60° C. Then 11.93 g (102.4 mmol) of trifluoroacetic acid in 30 ml of methylene chloride was added. Then the introduction of ozone began (25 l of $O_2$/h/0.6 A). As soon as the solution became greenish (excess of ozone), the feeding of ozone (30 minutes) was stopped. $N_2$ was passed through the solution for 15 minutes to drive out the excess ozone (solution became yellowish). Then 3.94 g (61.4 mmol) of dimethyl sulfide in 30 ml of methylene chloride was instilled in 10 minutes. It was stirred for 5 minutes more at 60° C. and then cooled with ice water to 0° C. Then 170 ml of methanol and in 20 minutes a solution of 34.31 g of titanium tetrachloride in 56 ml of methylene chloride were added. Then HCl gas and 5 minutes later $H_2S$ gas was introduced (yellow precipitate after a few minutes). The introduction of HCl and $H_2S$ were stopped after 3.5 hours. The flask was closed and allowed to stand overnight at room temperature. The reaction mixture was completely concentrated by evaporation. 200 ml of ether plus 200 ml of 1N HCl were added to the residue. 10.3 g (75 percent) of the subtitle product (noted above) was obtained as brownish oil from the organic phase. The crude product was dissolved in 250 ml of ether and then treated at 0° C. with HCl gas to produce the hydrochloride. 10.25 g (66 percent) of the subtitle compound (noted above) was obtained as hydrochloride. For the compound, the melting point (Mp) was 208° to 211° C.

What is claimed is:

1. 4-Oxo-3-(2-propenyl)-piperidine-3-carboxylic acid ester of the formula:

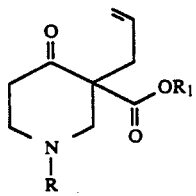

wherein R is hydrogen, a formyl group, an acetyl group or a benzoyl group or is a benzyl group, whose aromatic ring R is selected from the group consisting of hydrogen, formyl, acetyl, benzoyl, and benzyl, whose aromatic ring is optionally substituted by halogen, and $R_1$ is an alkyl group with 1 to 4 C atoms.

2. 4-Oxo-3-(2-propenyl)-piperidine of the formula:

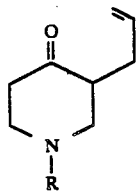

wherein R is hydrogen, a formyl group, an acetyl group or a benzoyl group or is a benzyl group, whose aromatic ring R is selected from the group consisting of hydrogen, formyl, acetyl, benzoyl, and benzyl, whose aromatic ring is optionally substituted by halogen, and $R_1$ is an alkyl group with 1 to 4 C atoms.

* * * * *